United States Patent [19]

Robeson et al.

[11] Patent Number: 5,120,818
[45] Date of Patent: Jun. 9, 1992

[54] CHAIN-EXTENDED POLY(ARYL ETHER KETONES)

[75] Inventors: Lloyd M. Robeson, Whitehouse Station; Paul A. Winslow, Warren; Markus Matzner, Edison; James E. Harris, Piscataway, all of N.J.; Louis M. Maresca, Pittsfield, Mass.

[73] Assignee: Amoco Corporation, Chicago, Ill.

[21] Appl. No.: 453,782

[22] Filed: Dec. 20, 1989

Related U.S. Application Data

[62] Division of Ser. No. 747,188, Jun. 21, 1985, Pat. No. 4,908,425.

[51] Int. Cl.⁵ ............ C08G 8/02; C08G 14/00; C08G 65/38
[52] U.S. Cl. ............ 528/125; 528/126; 528/128; 528/219
[58] Field of Search ............ 528/125, 126, 128, 219

[56] References Cited

U.S. PATENT DOCUMENTS

| | | | |
|---|---|---|---|
| 3,065,205 | 11/1962 | Bonner | 528/176 |
| 3,516,966 | 6/1970 | Berr | 528/179 |
| 4,056,511 | 11/1977 | Staniland | 528/174 |
| 4,108,837 | 8/1978 | Johnson et al. | 528/173 |
| 4,175,175 | 11/1979 | Johnson et al. | 528/128 |
| 4,229,564 | 10/1980 | Dahl | 528/128 |
| 4,247,682 | 1/1981 | Dahl | 528/128 |
| 4,275,186 | 6/1981 | Kawakami et al. | 528/174 |
| 4,320,224 | 3/1982 | Rose et al. | 528/125 |
| 4,611,033 | 9/1986 | Maresca | 528/486 |
| 4,645,819 | 2/1987 | Sterzel | 528/125 |
| 4,710,562 | 12/1987 | Maresca | 528/125 |
| 4,716,211 | 12/1987 | Clendinning et al. | 528/128 |
| 4,731,429 | 3/1988 | McMasters et al. | 528/127 |
| 4,820,790 | 4/1989 | Winslow et al. | 528/219 |

FOREIGN PATENT DOCUMENTS 0001879 5/1979 European Pat. Off. .
0030033 6/1981 European Pat. Off. .
2305456 3/1976 France .

*Primary Examiner*—John Kight, III
*Assistant Examiner*—P. Hampton-Hightower
*Attorney, Agent, or Firm*—Gary J. Cunningham; William H. Magidson; Frank J. Sroka

[57] ABSTRACT

This invention is directed to novel crystalline chain extended polymers containing segments of crystalline poly(aryl ether ketones). The novel materials are easy to prepare and display excellent toughness, fabricability and very good high temperature and solvent resistance.

4 Claims, No Drawings

CHAIN-EXTENDED POLY(ARYL ETHER KETONES)

This is a division of application Ser. No. 747,188, filed Jun. 21, 1985 now U.S. Pat. No. 4,908,425.

FIELD OF THE INVENTION

This invention is directed to novel crystalline chain extended polymers containing segments of crystalline poly(aryl ether ketones). The novel materials are easy to prepare and display excellent toughness, fabricability and very good high temperature and solvent resistance.

BACKGROUND OF THE INVENTION

Over the years, there has been developed a substantial body of patent and other literature directed to the formation and properties of poly(aryl ethers) (hereinafter called "PAE"). Some of the earliest work such as by Bonner, U.S. Pat. No. 3,065,205, involves the electrophilic aromatic substitution (e.g. Friedel-Crafts catalyzed) reaction of aromatic diacylhalides with unsubstituted aromatic compounds such as diphenyl ether. The evolution of this class to a much broader range of PAE's was achieved by Johnson et al., Journal of Polymer Science, A-1, vol. 5, 1967, pp. 2415–2427, Johnson et al., U.S. Pat. Nos. 4,108,837 and 4,175,175. Johnson et al. show that a very broad range of PAE can be formed by the nucleophilic aromatic substitution (condensation) reaction of an activated aromatic dihalide and an aromatic diol. By this method, Johnson et al. created a host of new PAE's including a broad class of poly(aryl ether ketones), hereinafter called "PAEK's".

In recent years, there has developed a growing interest in PAEKs as evidenced by Dahl, U.S. Pat. No. 3,953,400; Dahl et al., U.S. Pat. No. 3,956,240; Dahl, U.S. Pat. No. 4,247,682; Rose et al., U.S. Pat. No. 4,320,224; Maresca, U.S. Pat. No. 4,339,568; Atwood et al., Polymer, 1981, vol 22, August, pp. 1096–1103; Blundell et al., Polymer, 1983 vol. 24, August, pp. 953–958, Atwood et al., Polymer Preprints, 20, no. 1, April 1979, pp. 191–194; and Rueda et al., Polymer Communications, 1983, vol. 24, September, pp. 258–260. In early to mid-1970, Raychem Corp. commercially introduced a PAEK called STILAN ™, a polymer whose acronym is PEK, each ether and keto group being separated by 1,4-phenylene units. In 1978, Imperial Chemical Industries PLC (ICI) commercialized a PAEK under the trademark Victrex PEEK. As PAEK is the acronym of poly(aryl ether ketone), PEEK is the acronym of poly(ether ether ketone) in which the 1,4-phenylene units in the structure are assumed.

Thus PAEKs are well known; they can be synthesized from a variety of starting materials; and they can be made with different melting temperatures and molecular weights. The PAEKs are crystalline, and as shown by the Dahl and Dahl et al. patents, supra, at sufficiently high molecular weights they can be tough, i.e., they exhibit high values (>50 ft-lbs/in$^3$) in the tensile impact test (ASTM D-1822). They have potential for a wide variety of uses, but because of the significant cost to manufacture them, they are expensive polymers. Their favorable properties classes them in the upper bracket of engineering polymers.

PAEK's may be produced by the Friedel-Crafts catalyzed reaction of aromatic diacylhalides with unsubstituted aromatic compounds such as diphenyl ether as described in, for example, U.S. Pat. No. 3,065,205.

These processes are generally inexpensive processes; however, the polymers produced by these processes have been stated by Dahl et al., supra, to be brittle and thermally unstable. The Dahl patents, supra, allegedly depict more expensive processes for making superior PAEK's by Friedel-Crafts catalysis. In contrast, PAEK's such as PEEK made by nucleophilic aromatic substitution reactions are produced from expensive starting fluoro monomers and thus would be classed as expensive polymers.

THE INVENTION

The present invention is directed to chain extended poly(aryl ether ketone) polymers. The starting poly(aryl ether ketone) segments are prepared by the inexpensive Friedel-Crafts process using available and inexpensive raw materials. Coupling (chain-extension) of the oligomers is then carried out by nucleophilic polycondensation with a diphenol in the presence of a base. Products having superior toughness, good fabricability and excellent solvent and temperature resistance are obtained.

The polymers of the instant invention are prepared by the following processes:

Step 1

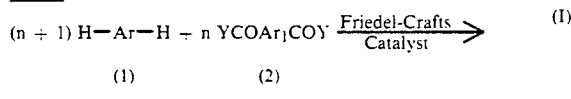

Step 2

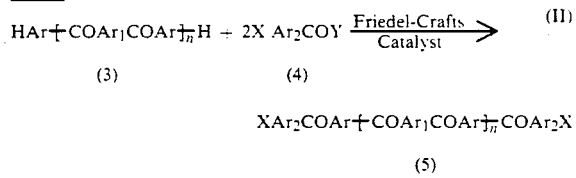

Step 3

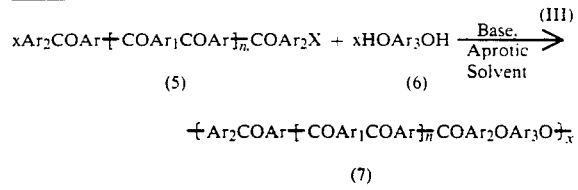

Alternatively, the polymers can be prepared by a slightly modified sequence as shown in the following equations (IV)–(VI).

Step 1

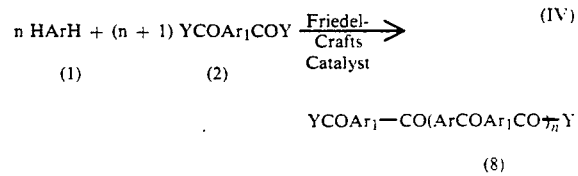

Step 2

-continued $$Y\text{COAr}_1-\text{CO[ArCOAr}_1\text{CO}]_n Y + 2X\text{ Ar}_2H \xrightarrow{\text{Friedel-Crafts}}_{\text{Catalyst}}$$ (V)

(8)  (9)

$$X\text{Ar}_2\text{COAr}_1+\text{COArCOAr}_1\text{CO}]_n\text{Ar}_2X$$

(10)

Step 3

$$x\text{Ar}_2\text{COAr}_1-\text{CO[ArCOAr}_1\text{CO}]_n\text{Ar}_2X +$$ (VI)

(10)

$$x\text{HOAr}_3\text{OH} \xrightarrow{\text{base}}_{\text{Aprotic Solvent}}$$

(11)

$$+\text{Ar}_2\text{COAr}_1-\text{CO[ArCOAr}_1\text{CO}]_n\text{Ar}_2\text{OAr}_3\text{O}]_x$$

(12)

In the equations above Ar and $Ar_1$ are divalent aromatic groups, $Ar_2$ is a divalent aromatic group wherein the substituents X and CO are in the para or otho position relative to each other, $Ar_3$ is a residue of a dihydric phenol, X is a halogen, preferably fluorine, Y is a halogen, preferably chlorine, n is an integer such that the molecular weight of the precursors (5) or (10) is below about 10,000 and x is one or greater.

The PAEK precursors of the types (5) and (10) as shown in the above equations may be produced by Friedel-Craft reactions utilizing hydrogen fluoride-boron trifluoride catalysts as described in, for example, U.S. Pat. Nos. 3,953,400, 3,441,538; 3,442,857 and 3,516,966.

Additionally, the precursors may be prepared by Friedel-Crafts processes as described in, for example, U.S. Pat. Nos. 3,065,205; 3,419,462; 3,441,538; 3,442,857; 3,516,966; and 3,666,612. In these patents a PAEK is produced by Friedel-Crafts polymerization techniques using Friedel-Crafts catalysts such as aluminum trichloride, zinc chloride, ferric bromide, antimony pentachloride, titanium tetrachloride, etc. and a solvent.

The precursor may also be prepared according to the processes as described in, for example, U.S. Defensive Publication T 103,703 and U.S. Pat. No. 4,396,755. In such processes, reactants such as (a) an aromatic monocarboxylic acid, (b) a mixture of at least one aromatic dicarboxylic acid, and an aromatic compound, and (c) combinations of (a) and (b) are reacted in the presence of a fluoroalkane sulphonic acid, particularly trifluoromethane sulphonic acid.

In all of the electrophilic routes described above, the precursor molecular weight is controlled using known techniques. The preparation may, for example, be conducted in a solvent where precipitation takes place after a given molecular weight is reached. Control of the reaction time is another method to control precursor size. Still another method and, by far, the simplest comprises adjusting the stoichiometry of the reaction mixture by using an appropriate excess of one of the reactants. Many other methods exist and are well known to those skilled in the art.

The term PAEK as used herein is meant to include homopolymers, copolymers, terpolymers, graft copolymers, and the like, provided crystallinity of the PAEK is maintained.

Specifically, the precursors may be prepared by reacting any of the well-known aromatic coreactants such as diphenyl sulfide, dibenzofuran, thianthrene, phenoxathin, dibenzodioxine, phenodioxin, diphenylene, 4,4'-diphenoxybiphenyl, xanthone, 2,2'-diphenoxybiphenyl, 1,4-diphenoxybenzene, 1,3-diphenoxybenzene, 1-phenoxynapthalene, 1,2-diphenoxynapthalene, diphenyl ether, 1,5-diphenoxynapthalene, and the like. Among these, diphenyl ether, diphenyl, diphenyl methane, 1,4-diphenoxy benzene, and 4,4'-diphenoxy diphenyl ether are preferred.

Similarly, the following compounds are diacyl halides which may be used as reactants: terephthaloyl chloride, isophthaloyl chloride, thio-bis(4,4'-benzoyl chloride), benzophenone-4,4'-di(carbonyl chloride), oxy-bis(3,3'-benzoyl chloride), diphenyl-3,3'-di(carbonyl chloride), carbonyl-bis(3,3'-benzoyl chloride), sulfonyl-bis(4,4'-benzoyl chloride), sulfonyl-bis(3,3'-benzoyl chloride), sulfonyl-bis(3,4'-benzoyl chloride), thio-bis(3,4'-benzoyl chloride), diphenyl-3,4'-di(carbonyl chloride), oxy-bis[4,4'-(2-chlorobenzoyl chloride)], naphthalene-1,6-di(carbonyl chloride), naphthalene-1,5-di(carbonyl chloride), naphthalene-2,6-di(carbonyl chloride), oxy-bis[7,7'-naphthalene-2,2'-di(carbonyl chloride)], thio-bis[8,8'-naphthalene-1,1-di(carbonyl chloride)], [7,7'-binaphthyl-2,2'-di(carbonyl chloride)], diphenyl-4,4'-di(carbonyl chloride), carbonyl-bis[7,7'-naphthalene-2,2'-di(carbonyl chloride)], sulfonyl-bis[6,6'-naphthalene-2,2'-di(carbonyl chloride)], dibenzofuran-2,7-di(carbonyl chloride) and the like.

Illustrative of suitable acyldihalides include carbonyl chloride (phosgene), carbonyl bromide, carbonyl fluoride and oxaloyl chloride.

Preferably, diphenyl ether and/or diphenoxybenzene are reacted with terephthaloyl chloride and/or phosgene.

Preferred end-capping agents $$X\text{Ar}_2\text{COY} \text{ and } X\text{Ar}_2H$$

(4)  (9)

are p-fluorobenzoyl chloride and fluorobenzene. It should be noted that other similar aromatic compounds. e.g.

(13)

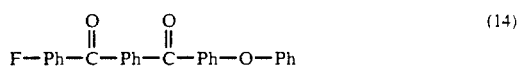

(14)

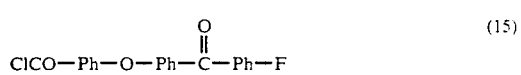

(15)

(16)

and materials wherein the fluoride is replaced by chloride, bromide, or nitro can be similarly used.

(Note Ph is a phenyl or a 1,4-phenylene unit with the proviso that where there are two carbonyl groups attached to the same phenyl ring, up to 50% of these groups may be in the 1,3 position to each other).

In another embodiment, the self condensation of the following halo-aromatic halides

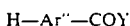

wherein Ar" is a divalent aromatic radical and H is an aromatically bound hydrogen atom, Y is as defined above, and COY is an aromatically bound acyl halide group which monoacyl halide is self-polymerizable, offers yet another route to these halo-terminated precursors; an example follows:

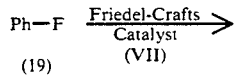

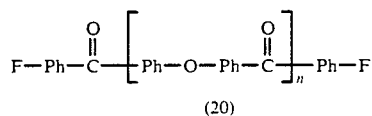

The preferred precursors are those of formulae (20), (21), (22), and (23).

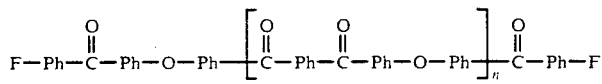

(21)

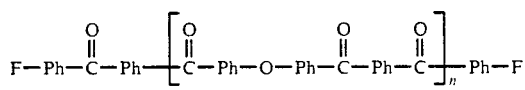

(22)

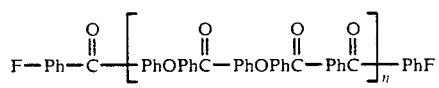

(23)

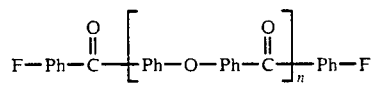

(23a)

(23b)

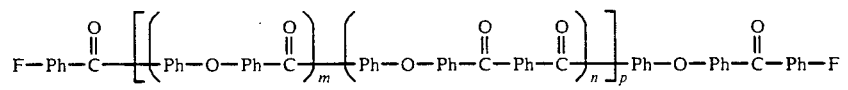

The preferred Friedel-Crafts catalysts are aluminum chloride, antimony pentachloride and ferric chloride. Other Friedel-Crafts catalysts, such as aluminum bromide, boron trifluoride, boron trifluoride/hydrogen fluoride, zinc chloride, antimony trichloride, ferric bromide, titanium tetrachloride, and stannic chloride, can also be used.

The reaction is generally carried out in the presence of a solvent. The preferred organic solvent is 1,2-dichloroethane. Other solvents such as symmetrical tetrachloroethane, o-dichlorobenzene hydrogen fluoride, or carbon disulfide may be employed.

It is often advantageous to add to the condensation mixture Lewis acid complexing reagents which moderate the reaction and avoid the formation of undesirable secondary products. Typical of such complexing agents are co-solvents such as nitromethane, nitropropane, N, N-dimethyl formamide, sulfolane, and the like. Salts capable of complexation, such as lithium chloride can also be used.

The reaction may be carried out over a range of temperatures which are from about −40° C. to about 160° C. In general, it is preferred to carry out the reaction at temperatures in the range of 0° to 30° C. In some cases it is advantageous to carry out the reaction at temperatures above 30° C. or below 0° C. The reaction may be carried out at atmospheric pressure although higher or lower pressures may be used.

It should be noted that the preparation of the oligomers (5) and (10) can be performed via a series of separate steps as indicated in equations I-IV. It is also possible, however to prepare these intermediates by an in-situ process, i.e., by charging all of the ingredients ((1), (2), and (4) or (9)) into the reaction vessel simultaneously producing the oligomeric precursor directly in one step.

The chain-extended poly(aryl ether ketones) (7) and (12) are prepared by the nucleophilic polycondensation of the precursors as described above with a diphenol. Preferred diphenols are either mononuclear such as hydroquinone, or polynuclear such as the structures (24)-(28) shown below.

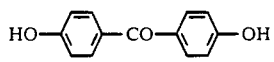

(24)

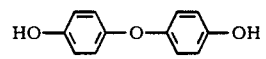

(25)

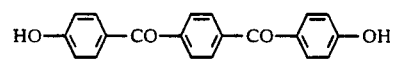

(26)

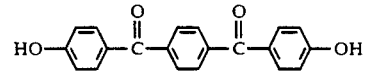

(26a)

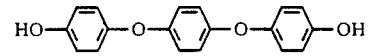

(27)

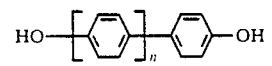

(28)

-continued where n is 1 to 3

Other materials also termed appropriately "bisphenols" are also highly valuable and preferred. These materials are the bisphenols of a symmetrical or unsymmetrical joining group, the latter, for example, being an ether oxygen (—O—), carbonyl

sulfone

or hydrocarbon residue in which the two phenolic nuclei are joined to the same or different carbon atoms of the residue.

Such dinuclear phenols can be characterized as having the structure:

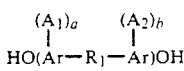

wherein Ar is a divalent aromatic group and preferably is a phenylene group, $A_1$ and $A_2$ can be the same or different inert substituent groups such as alkyl groups having from 1 to 4 carbons atoms, halogen atoms, i.e., fluorine, chlorine bromine or iodine, or alkoxy radicals having from 1 to 4 carbon atoms, a and b are integers having a value of from 0 to 4, inclusive, and $R_1$ is representative of a bond between aromatic carbon atoms as in a dihydroxy-diphenyl, such as 4,4', 3,3', or 4,3'-dihydroxydiphenyl; or is a divalent radical, including, for example, radicals such as

—O—, —S—, —SO—, —S—S—, —SO₂, and divalent hydrocarbon radicals such as alkylene, alkylidene, cycloalkylene, cycloalkylidene, or the halogen, alkyl, aryl or like substituted alkylene, alkylidene and cycloaliphatic radicals or an aromatic radical; it may also represent rings fused to both Ar groups.

Examples of specific dihydric polynuclear phenols include among other the bis-(hydroxyphenyl) alkanes such as 2,2-bis-(4-hydroxyphenyl)propane, 2,4'-dihydroxydiphenylmethane, bis-(2-hydroxyphenyl)methane, bis-(4-hydroxyphenyl)methane, bis(4-hydroxy-2,6-dimethyl-3-methoxyphenyl)methane, 1,1-bis-(4-hydroxyphenyl)ethane, 1,2-bis-(4-hydroxyphenyl)ethane, 1,1-bis-(4-hydroxy-2-chlorophenyl)ethane, 1,1-bis-(3-methyl-4-hydroxyphenyl)propane, 1,3-bis-(3-methyl-4-hydroxyphenyl)propane, 2,2-bis-(3-phenyl-4-hydroxyphenyl)propane, 2,2-bis-(3-isopropyl-4-hydroxyphenyl)propane, 2,2-bis-(2-isopropyl-4-hydroxyphenyl)propane, 2,2-bis-(4-hydroxynaphthyl)propane, 2,2-bis-(4-hydroxyphenyl)pentane, 3,3-bis-(4-hydroxyphenyl)pentane, 2,2-bis-(4-hydroxyphenyl)heptane, bis-(4-hydroxyphenyl)phenylmethane, 2,2-bis-(4-hydroxyphenyl)-1-phenyl-propane, 2,2-bis-(4-hydroxyphenyl)1,1,1,3,3,3,-hexafluoropropane, and the like;

di(hydroxyphenyl)sulfones such as bis-(4-hydroxyphenyl)sulfone, 2,4'-dihydroxydiphenyl sulfone, 5-chloro-2,4-dihydroxydiphenyl sulfone, 5'-chloro-4,4'-dihydroxydiphenyl sulfone, and the like;

di(hydroxyphenyl)ethers such as bis-(4-hydroxyphenyl)ether, the 4,3'-, 4,2'-2,2'-2,3'-, dihydroxydiphenyl ethers, 4,4'dihydroxy-2,6-dimethyldiphenyl ether, bis(4-hydroxy-3-isobutylphenyl)ether, bis-(4-hydroxy-3-isopropylphenyl)ether, bis-(4-hydroxy-3-chlorophenyl)ether, bis-(4-hydroxy-3-fluorophenyl)ether, bis-(4-hydroxy-3-bromophenyl)ether, bis-(4-hydroxynaphthyl)ether, bis-(4-hydroxy-3-chloronaphthyl)ether, and 4,4'-dihydroxy-3,6-dimethoxydiphenyl ether.

Finally, the dihydric derivatives of polynuclear hydrocarbons such as the dihydroxynapthalenes (e.g., 1,4-dihydroxynaphthalene, 1,5-dihydroxynaphthalene, 2,7-dihydroxynaphthalene, and the like) and dihydroxyanthracenes and dihydroxyphenanthrenes are also useful. Note that mixtures of the difluoro-terminated precursors and/or mixtures of the diphenols can also be used for the purpose of the instant invention. Moreover, the reactions can be performed with the isolation and purification of the intermediate or in a one-pot scheme wherein the precursor is reacted with the diphenol(s) directly after preparation without being isolated.

The reactions are carried out by heating a mixture of the said precursor or precursors with the appropriate diphenol or diphenols at a temperature of from about 100° to about 400° C.

European Patent Application 125,816, filed Apr. 19, 1984, based for priority upon British Patent Application 8,313,110, filed May 12, 1983, is directed to a method for increasing the molecular weight by melt polymerization of a poly(aryl ether) such as PEEK.

The process of European Patent Application 125,816, provides a basis by melt polymerization above the crystalline melting point of the poly(aryl ether) to increase the molecular weight by chain extension of polymer blocks. The application theorizes that the procedures can be used for making the block copolymers described in U.S. Pat. Nos. 4,052,365 and 4,268,635. Implicit problems associated in the process of this application are the difficulty in controlling the molecular weight of the resulting polymer and/or limiting isomerization and the problems associated with branching. The process of this European application would appear to be advantageous in making composites where the linearity and solution properties of the final polymer are not so critical.

The reactions are conducted in the presence of an alkali metal carbonate or bicarbonate. Preferably a mixture of alkali metal carbonates or bicarbonates is used. When a mixture of alkali metal carbonates or bicarbonates is used, the mixture comprises sodium carbonate or bicarbonate with a second alkali metal carbonate or bicarbonate wherein the alkali metal of the second carbonate or bicarbonate has a higher atomic number than that of sodium. The amount of the second alkali metal carbonate or bicarbonate is such that there is from 0.01 to about 0.25 gram atoms of the second alkali metal per gram atom of sodium.

The higher alkali metal carbonates or bicarbonates are thus selected from the group consisting of potassium, rubidium and cesium carbonates and bicarbonates. Preferred combinations are sodium carbonate or bicarbonate with potassium carbonate or cesium carbonate.

The alkali metal carbonates or bicarbonates should be anhydrous although, if hydrated salts are employed, where the polymerization temperature is relatively low, e.g. 100° to 250° C., the water should be removed, e.g. by heating under reduced pressure, prior to reaching the polymerization temperature.

Where high polymerization temperatures (>250° C.) are used, it is not necessary to dehydrate the carbonate or bicarbonate first as any water is driven off rapidly before it can adversely affect the course of the polymerization reaction.

The total amount of alkali metal carbonate or bicarbonate employed should be such that there is at least 1 atom of alkali metal for each phenol group.

An excess of carbonate or bicarbonate may be employed. Hence there may be 1 to 1.2 atoms of alkali metal per phenol group. While the use of an excess of carbonate or bicarbonate may give rise to faster reactions, there is the attendant risk of cleavage of the resulting polymer, particularly when using high temperatures and/or the more active carbonates.

As stated above the amount of the second (higher) alkali metal carbonate or bicarbonate employed is such that there are 0.01 to about 0.25 grams atoms of the alkali metal of higher atomic number per gram atom of sodium.

Thus when using a mixture of carbonates, e.g. sodium carbonate and cesium carbonate, there should be 0.1 to about 20 moles of cesium carbonate per 100 moles of sodium carbonate. Likewise when using a mixture of a bicarbonate and a carbonate, e.g. sodium bicarbonate and potassium carbonate, there should be 0.05 to 10 moles of potassium carbonate per 100 moles of sodium bicarbonate.

A mixed carbonate, for example sodium and potassium carbonate, may be employed as the second alkali metal carbonate. In this case, where one of the alkali metal atoms of the mixed carbonate is sodium, the amount of sodium in the mixed carbonate should be added to that in the sodium carbonate when determining the amount of mixed carbonate to be employed.

Preferably, from 0.005 to 0.1 gram atoms of the alkali metal of the second alkali metal carbonate or bicarbonate per gram atom of sodium is used.

The bisphenol and the precursor compound should be used in substantially equimolar amounts. An excess of one over the other leads to the production of lower molecular weight products. However a slight excess, up to 5 mole %, of the dihalide or diphenol may be employed if desired.

The reaction is carried out in the presence of an inert solvent.

The solvent employed is preferably an aliphatic or aromatic sulfoxide or sulfone of the formula

R—S(O)$_t$—R' where t is 1 or 2 and R and R' are alkyl or aryl groups and may be the same or different. R and R' may together form a divalent radical. Preferred solvents include dimethyl sulfoxide, dimethyl sulfone, sulfolane (1,1 dioxothiolan), or aromatic sulfones of the formula:

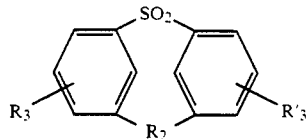

where $R_2$ is a direct link, an oxygen atom or two hydrogen atoms (one attached to each benzene ring) and $R_3$ and $R'_3$, which may be the same or different, are hydrogen atoms and alkyl or phenyl groups. Examples of such aromatic sulfones include diphenylsulfone, dibenzothiophen dioxide, phenoxathiin dioxide and 4-phenylsulfonyl biphenyl. Diphenylsulfone is the preferred solvent. Other solvents that may be used include N,N-dimethyl acetamide, N,N-dimethyl formamide and N-methyl-2-pyrrolidone.

The polymerization temperature is in the range of from about 100° to about 400° C. and will depend on the nature of the reactants and the solvent, if any, employed. The preferred temperature is above 270° C. The reactions are generally performed under atmospheric pressure. However, higher or lower pressures may be used.

For the production of some polymers, it may be desirable to commence polymerization at one temperature, e.g. between 200° and 250° C. and to increase the temperature as polymerization ensues. This is particularly necessary when making polymers having only a low solubility in the solvent. Thus, it is desirable to increase the temperature progressively to maintain the polymer in solution as its molecular weight increases.

To minimize cleavage reactions it is preferred that the maximum polymerization temperature be below 350° C.

The polymerization reaction may be terminated by mixing a suitable end-capping reagent, e.g. a mono- or polyfunctional halide such as methyl chloride, t-butyl chloride or 4,4'-dichlorodiphenylsulfone with the reaction mixture at the polymerization temperature, heating for a period of up to one hour at the polymerization temperature and then discontinuing the polymerization.

This invention is also directed to preparing poly(aryl ether ketone) chain-extended polymers by the reaction of a mixture of at least one bisphenol and at least one dihalobenzenoid compound in the presence of a combination of sodium carbonate and/or bicarbonate and an alkali metal halide selected from potassium, rubidium, or cesium fluoride or chloride, or combinations thereof.

The reaction is carried out by heating a mixture of one or more bisphenols and one or more of the halo-terminated precursors, as described herein, at a temperature of from about 100° to about 400° C. in solution. The reaction is conducted in the presence of added sodium carbonate and/or bicarbonate and potassium, rubidium or cesium fluorides or chlorides. The sodium carbonate or bicarbonate and the chloride and fluoride salts should be anhydrous although, if hydrated salts are employed, where the reaction temperature is relatively low, e.g. 100° to 250° C., the water should be removed, e.g. by heating under reduced pressure, prior to reaching the reaction temperature.

Where high reaction temperatures (>250° C.) are used, it is not necessary to dehydrate the carbonate or bicarbonate first as any water is driven off rapidly before it can adversely affect the course of the reaction. Optionally, an entraining organic medium can be used to remove water from the reaction such as toluene, xylene, chlorobenzene, and the like.

The total amount of sodium carbonate or bicarbonate and potassium, rubidium or cesium fluoride or chloride, or combinations thereof employed should be such that there is at least 1 atom of total alkali metal for each phenol group, regardless of the anion (carbonate, bicarbonate or halide).

Preferably, from about 1 to about 1.2 atoms of sodium for each phenol group is used. In another preferred embodiment from 0.001 to about 0.5 atoms of alkali metal (derived from a higher alkali metal halide) is used for each phenol group.

The sodium carbonate or bicarbonate and potassium fluoride are used such that the ratio of potassium to sodium therein is from about 0.001 to about 0.5, preferably from about 0.01 to about 0.25, and most preferably from about 0.02 to about 0.20.

An excess of total alkali metal may be employed. Hence there may be about 1 to about 1.7 atoms of alkali metal per phenol group. While the use of a large excess of alkali metal may give rise to faster reactions, there is the attendant risk of cleavage of the resulting polymer, particularly when using high temperatures and/or the more active alkali metal salts. Of course it is well known to those skilled in the art that cesium is a more active metal and potassium is a less active metal so that less cesium and more potassium are used. Further, the chloride salts are less active than the fluoride salts so that more chloride and less fluoride is used.

The bisphenol or bisphenols and the dihalo-terminated precursor or precursors should be used in substantially equimolar amounts when maximum molecular weight is sought. However a slight excess, up to 5 mole %, of the dihalide or of the bisphenol may be employed if desired. An excess of one over the other leads to the production of low molecular weight products which can be desirable when the process is directed to making lower molecular weight PAEK.

The reaction is carried out in the presence of an inert solvent as described above.

The reaction temperature is in the range of from about 100° to about 400° C. and will depend on the nature of the reactants and the solvent, if any, employed. The preferred temperature is above 250° C. The reactions are preferably carried out at ambient pressure. However, higher or lower pressure can also be used. The reaction is generally carried out in an inert atmosphere.

For the production of some chain-extended polymers it may be desirable to commence reaction at one temperature, e.g. between 200° and 250° C. and to increase the temperature as reaction ensues. This is particularly necessary when making high molecular weight polymers having only a low solubility in the solvent. Thus, there it is desirable to increase the temperature progressively to maintain the polymer in solution as its molecular weight increases.

The polymers of this invention may be blended with one or more other polymers such as polyarylates, polysulfones, polyetherimides, polyamideimides, polyimides, polyphenylene sulfides, polyesters, polycarbonates, polyamides, polyhydroxyethers and the like.

The polymers of this invention may include mineral fillers such as carbonates including chalk, calcite and dolomite; silicates including mica, talc, wollastonite; silicon dioxide; glass spheres; glass powders; aluminum; clay; quartz; and the like. Also, reinforcing fibers such as fiberglass, carbon fibers, and the like may be used. The polymers may also include additives such as titanium dioxide; thermal stabilizers, ultraviolet light stabilizers, plasticizers, and the like.

The polymers of this invention may be fabricated into any desired shape, i.e., moldings, coatings, films, or fibers. They are particularly desirable for use as electrical insulation for electrical conductors.

Also, the polymers may be woven into monofilament threads which are then formed into industrial fabrics by methods well known in the art as exemplified by U.S. Pat. No. 4,359,501. Further, the copolymers may be used to mold gears, bearings and the like.

EXAMPLES

The following examples serve to give specific illustrations of the practice of this invention but they are not intended in any way to limit the scope of this invention.

EXAMPLE 1

A 250 ml glass resin reactor was equipped with a mechanical stirrer, nitrogen sparge tube, thermocouple probe, Dean-Stark trap reflux condenser and a pressure equalizing dropping funnel. To the reactor were charged 3.08 g (0.028 moles) of hydroquinone, 0.20 g (0.001 moles) of potassium carbonate, 2.88 g (0.027 moles) of sodium carbonate, 28.56 g of a difluoro end capped crystalline poly(aryl ether ketone) having the general structural formula (29),

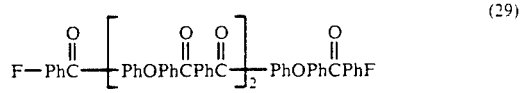

(29)

76 g of diphenyl sulfone and xylene. The apparatus was evacuated then charged with nitrogen. This procedure was repeated 3 additional times. While being continuously purged with nitrogen the mixture was heated to 110° C. for 10 minutes. The reaction was carried out at a temperature of 320° C. resulting in a viscous mixture which was poured from the reactor, allowed to solidify and then ground finely. The product was refluxed in acetone (700 ml), followed by an aqueous hydrochloric acid solution (700 ml). It was then washed with water (2 times using 500 ml) and acetone (2 times using 500 ml) at room temperature. The product was dried in a vacuum oven at 100° C. for 24 hours. The final polymer having a general structural formula (30) had a reduced viscosity of 1.67 dl/g (in concentrated sulfuric acid at 1 g/100 ml and 25° C.).

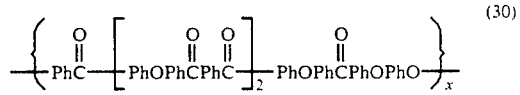

(30)

EXAMPLE 2

Example 1 was repeated and a polymer having a reduced viscosity of 1.76 dl/g was obtained.

EXAMPLE 3

Example 1 was repeated and a polymer having a reduced viscosity of 0.96 dl/g was obtained.

EXAMPLE 4

Example 1 was repeated and a polymer having a reduced viscosity of 1.32 dl/g was obtained.

EXAMPLE 5

A 250 ml flask was fitted with a mechanical stirrer, nitrogen sparge tube, thermocouple probe, Dean-Stark trap, reflux condenser and a pressure equalizing dropping funnel. To the apparatus were charged 2.94 g (0.0267 moles) of hydroquinone, 2.89 g (0.0273 moles) of sodium carbonate, 68 g of diphenyl sulfone and 30.0 g of a oligomeric poly(aryl ether ketone) having the structural formula (29).

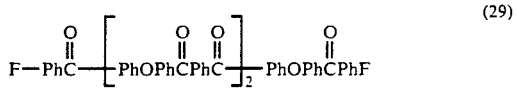
(29)

The apparatus was purged with nitrogen then evacuated. This procedure was repeated 4 additional times. While being continuously purged with nitrogen, 30 ml of xylene was added and the mixture heated to 120° C. for 1 hour. The resultant mixture was heated to 320° C. during which time the xylene was continuously being replenished. A reaction temperature of 320° C. was maintained for 3.5 hours, after which the viscous mixture was poured into a stainless steel pan, allowed to solidify, and then ground finely. The product was refluxed in acetone (700 ml), in aqueous hydrochloric acid solution (700 ml), and washed in a blender with water (2 times using 500 ml), acetone (2 times using 500 ml), filtered then dried in a vacuum for 24 hours at 100° C. The final polymer had the general structural formula (30) and a reduced viscosity of 0.99 dl/g as measured in concentrated sulfuric acid (1 g/100 ml) at 25° C.

meric poly(aryl ether ketone) having the structural formula (29).

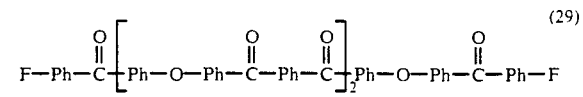
(29)

The apparatus was evacuated, purged with nitrogen (5 times) and while under a positive flow of nitrogen was charged with 30 ml of xylene and heated to 120° C. After 1 hour the mixture was heated to 320° C., during which time the distilling xylene was continuously replenished. The resultant viscous solution was poured into a stainless steel pan, allowed to solidify and then ground finely. The product was then refluxed in acetone (700 ml), in aqueous hydrochloric acid solution (700 ml) and washed in a blender with water (2 times using 500 ml), acetone (2 times using 500 ml), filtered and dried in a vacuum for 24 hours at 100° C. The final polymer had the general structural formula (31) and a reduced viscosity of 1.17 dl/g as measured in concentrated sulfuric acid (1g/100 ml) at 25° C.

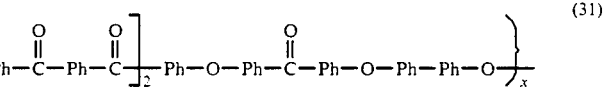
(31)

The polymer was compression molded (20 mil) and tested for tensile strength and modulus according to ASTM-D-638, yield elongation and elongation at break according to ASTM-D-638 and pendulum impact strength according to ASTM-D-256.

The melt flow ration $MF_{30}/MF_{10}$ was measured by heating a plug of polymer in a Tinius Olsen Thermodyne (melt flow cell) at 350°. The polymer was added to the preheated chamber of the thermodyne and put under a constant pressure of 44 psi. After 10 and 30 minutes, samples of polymer were taken by allowing the polymer to flow freely from the bottom of the cavity.

The results are as follows:

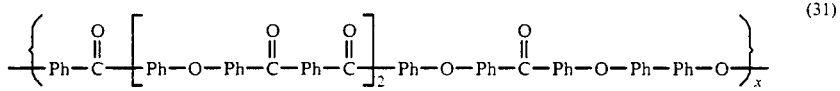
(30)

| | |
|---|---|
| Melt flow ratio | 0.79 |
| Tensile strength (psi) | 13.700 |
| Tensile modulus (psi) | 358.000 |
| Yield elongation (%) | 7.5 |
| Break elongation (%) | 15.5 |
| Pendulum Impact (ft-lb/in$^3$) | 71 |

EXAMPLE 6

Example 5 was repeated using the following stoichiometric proportions: 2.97 g (0.0270 moles) of hydroquinone, 2.92 g (0.275 moles) of sodium carbonate, 68 g of diphenyl sulfone and 30.0 g of an oligomeric poly(aryl ether ketone) having the structural formula (29). The resultant polymer having the general structural formula (30) had a reduced viscosity of 1.04 dl/g as measured in concentrated sulfuric acid (1 g/100 ml) at 25° C.

EXAMPLE 7

A 250 ml flask was fitted with a mechanical stirrer, nitrogen sparge tube, thermocouple probe, Dean-Stark trap, reflux condenser and a pressure equalizing dropping funnel. The apparatus was charged with 4.17 g (0.0224 moles) of 4,4'-biphenol, 2.30 g (0.0217 moles) of sodium carbonate, 0.16 g (0.0011 moles) of potassium carbonate, 61 g of diphenyl sulfone and 25 g of an oligo-

EXAMPLE 8

A 250 ml flask was fitted with a mechanical stirrer, nitrogen sparge tube, thermocouple probe, Dean-Stark trap reflux condenser and a pressure equalizing dropping funnel. The apparatus was charged with 5.60 g (0.0224 moles) of 4,4'-sulfonyl diphenol, 2.30 g (0.0217 moles) of sodium carbonate, 0.16 g (0.0011 moles) of potassium carbonate, 65 g of diphenyl sulfone, and 25 g of an oligomeric polyarylether ketone having the structural formula (29).

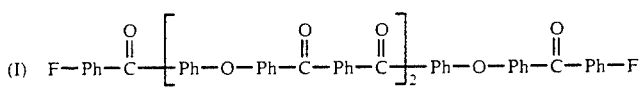

(I)

The apparatus was evacuated then purged with nitrogen (5 times) and while under a positive flow was charged with 30 ml of xylene and heated to 120° C. After 1 hour the mixture was heated to 320° C., during which time the distilling xylene was continuously replenished. The resultant viscous solution was poured into a stainless steel pan, allowed to solidify and then ground finely. The product was then refluxed in acetone (700 ml), in aqueous hydrochloric acid solution (700 ml) and washed in a waring blender with water (2 times using 500 ml), acetone (2 times using 500 ml), filtered and dried in vacuo for 24 hours at 100° C. The final polymer had the general structural formula (32) and a reduced viscosity of 1.55 dl/g in concentrated sulfuric acid (1 g/100 ml) at 25° C.

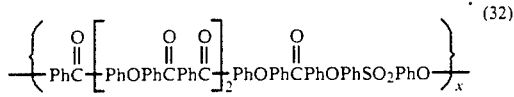

(32)

The polymer was tested as in Example 7. The results are as follows:

| Melt flow ratio | 0.17 |
| --- | --- |
| Tensile strength (psi) | 14,700 |
| Tensile modulus (psi) | 322,000 |
| Yield elongation (%) | 7.7 |
| Break elongation (%) | 9.0 |
| Pendulum Impact (ft-lb/in$^3$) | 66.0 |

Example 9 to 15 illustrate the preparation of selected precursors.

EXAMPLE 9

A 1000 ml flask was fitted with a mechanical stirrer, nitrogen sparge tube, thermometer, reflux condenser and gas outlet connected to an aqueous sodium hydroxide trap. The apparatus was purged with nitrogen and while under a positive pressure was charged with 700 ml of 1,2-dichloroethane, 1.02 g (0.005 moles) of isphthaloy chloride, 19.28 g (0.095 moles) of terephthaloyl chloride, 17.87 g (0.105 moles) of diphenyl ether, 1.59 g (0.010 moles) of p-fluorobenzoyl chloride, and 50.47 g (0.420 moles) of sulfolane. The mixture was cooled to 0° C. as 98.00 g (0.735 moles) of aluminum trichloride was added at such a rate as not to exceed 5° C. After 6 hours at 0° C. the deep red solution was allowed to warm to room temperature and stirring continued for an additional 17 hours. The entire reaction mixture was poured into dilute aqueous acid (3000 ml water/100 ml hydrochloric acid conc.) and heated to reflux for 2 hours while the 1,2-dichloroethane was continuously removed. The final polymer was filtered and dried in a vacuum at 60° C. for 24 hours to give 30.60 grams of the final polymer having a reduced viscosity of 0.35 dl/g as measured in concentrated sulfuric acid (1 g/100 ml) at 25° C.

The polymer was tested in Example 7.
The results are as follows:

| Melt flow ratio | 0.17 |
| --- | --- |
| Tensile strength (psi) | 14,700 |
| Tensile modulus (psi) | 322,000 |
| Yield elongation (%) | 7.7 |
| Break elongation (%) | 9.0 |
| Pendulum Impact (ft-lb/in$^3$) | 66.0 |

EXAMPLE 10

A 500 ml flask was fitted with a mechanical stirrer, nitrogen sparge tube, thermometer, reflux condenser and gas outlet connected to an aqueous sodium hydroxide trap. The apparatus was purged with nitrogen and while under a positive pressure of nitrogen was charged with 11.40 g (0.067 moles) of diphenyl ether, 20.30 g (0.100 moles) of terephthaloyl chloride and 270 ml of fluorobenzene. The mixture was cooled to 0° C. as 34.67 g (0.260 moles) of aluminum trichloride was added at such a rate as not to exceed 5° C. After stirring at 0° C. for 6 hours the reaction mixture was allowed to warm to 25° C. and stirring continued for an additional 17 hours. The resultant reaction mixture was poured into dilute aqueous acid (3000 ml water/100 ml hydrochloric acid conc.) and refluxed with continuous removal of the excess fluorobenzene. The resultant precipitate was filtered, refluxed in 5% hydrochloric acid (700 ml), filtered, washed with water (2 times using 500 ml), followed by methanol (2 times using 500 ml) at room temperature and dried in a vacuum at 100° C. for 24 hours. The final oligomeric crystalline poly(aryl ether ketone) having structural formula (33) was identified by $^{13}$C NMR and confirmed by mass spectroscopy.

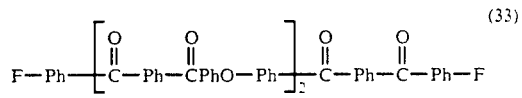

(33)

EXAMPLE 11

A 500 ml flask was fitted with a mechanical stirrer, reflux condenser, nitrogen sparge tube, thermometer and gas outlet connected to an aqueous sodium hydroxide trap. The apparatus was purged with nitrogen and while under a positive pressure was charged with 220 ml of 1,2-dichloroethane, 27.20 g (0.134 moles) of terephthaloyl chloride, 34.04 g (0.200 moles) of diphenyl ether, 21.25 g (0.134 moles) of p-fluorobenzoyl chloride, and 96.62 g (0.804 moles) of sulfolane. The mixture was cooled to 0° C. as 187.61 g (1.407 moles) of aluminum trichloride was added at such a rate as not to exceed 5° C. After 6 hours at 0° C., the viscous homogeneous reaction mixture was allowed to warm to room temperature and stirring continued for an additional 17 hours. The entire mixture was then poured into dilute aqueous acid (3000 ml water/100 ml hydrochloric acid conc.) and heated to reflux for 2 hours while the 1,2-dichlroethane was continuously removed. The resultant precipitate was collected via filtration then added to 5% hydrochloric acid and refluxed for 2 hours, filtered, washed in a blender with water (2 times using 500 ml)

and methanol (2 times using 500 ml, then dried in a vacuum at 100° C. for 24 hours. The final oligomer having structure formula (29) was characterized by $^{13}$C NMR and confirmed by mass spectroscopy and chemical analysis.

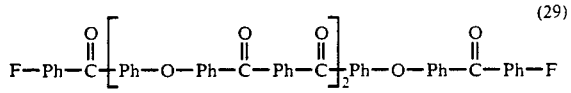

(29)

EXAMPLE 12

A 500 ml flask was fitted with a mechanical stirrer, reflux condenser, thermometer, nitrogen sparge tube, and gas outlet fitted to an aqueous sodium hydroxide trap. The apparatus was charged with 185 ml of o-dichlorbenzene, 34.04 g (0.20 moles) of diphenyl ether, 27.20 g (0.134 moles) of terephthaloyl chloride, 21.25 g (0.134 moles) of p-fluorobenzoyl chloride and 29.39 g (0.402 moles) of N N-dimethyl formamide. The mixture was cooled to 0° C. as 139.37 g (1.045 moles) of aluminum trichloride was added at such a rate as not to exceed 20° C. After completion of the addition the mixture was warmed to room temperature and stirring continued for an additional 17 hours. The entire mixture was then added to stirring methanol (1.5 l), filtered, added to dilute aqueous acid (3000 ml water/100 ml hydrochloric acid conc.) and refluxed for 2 hours. The resultant precipitate was collected via filtration and washed in a blender with water (2 times 500 ml), methanol (2 times 500 ml); filtered and dried in a vacuum at 100° C. for 24 hours. The final oligomer having the structural formula (29) was characterized by $^{13}$C NMR and confirmed by mass spectroscopy.

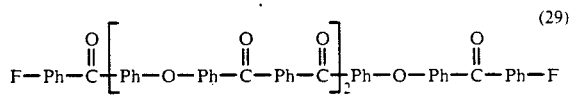

(29)

EXAMPLE 13

A 100 ml flask was fitted with a mechanical stirrer, reflux condenser, thermometer, nitrogen sparge, and gas outlet connected to an aqueous sodium hydroxide trap. The apparatus was purged with nitrogen and while under a positive pressure was charged with 17.02 g (0.100 moles) of diphenyl ether, 10.15 g (0.050 moles) of terephthaloyl chloride, 15.86 g (0.100 moles) of p-fluorobenzoyl chloride and 48 mls of 1,2-dichloroethane. The mixture was cooled to 0° C. as 34.67 g (0.260 moles) of aluminum trichloride was added at such a rate as not to exceed 5° C. After 6 hours at 0° C. the viscous homogeneous mixture was allowed to warm to room temperature and stirring continued for an additional 17 hours. The entire mixture was then poured into dilute aqueous acid (1300 ml water/50 ml hydrochloric acid conc.), refluxed with continuous removal of 1,2-dichloroethane and filtered. The precipitate was refluxed in 5% hydrochloric acid (700 ml), filtered, washed at room temperature with water (2 times using 500 ml) and methanol (2 times using 500 ml) and dried in a vacuum at 100° C. for 24 hours. The final oligomeric crystalline poly(aryl ether ketone) having the structural formula (34) was characterized by $^{13}$C NMR and confirmed by mass spectroscopy and elemental analysis.

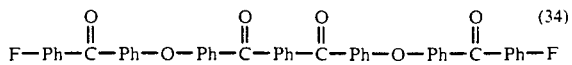

(34)

EXAMPLE 14

A 250 ml flask was fitted with a mechanical stirrer, nitrogen sparge tube, thermometer, reflux condenser, and gas outlet connected to an aqueous sodium hydroxide trap. The apparatus was purged with nitrogen and while under a positive pressure was charged with 96 ml of 1,2-dichloroethane, 11.40 g (0.067 moles) of diphenyl ether, 20.30 g (0.100 moles) of terephthaloyl chloride and 6.44 g (0.067 moles) of fluorobenzene. The mixture was cooled to 0° C. as 34.67 g (0.260 moles) of aluminum trichloride was added at such a rate as not to exceed 5° C. After 6 hours at 0° C. the heterogeneous slurry was allowed to warm to room temperature and stirring continued an additional 17 hours. The entire mixture was then poured into dilute aqueous acid (3000 ml water/100 ml hydrochloric acid conc.) and refluxed for 2 hours with the continuous removal of 1,2-dichloroethane. The resultant precipitate was collected via filtration refluxed in 5% hydrochloric acid (700 ml), filtered, washed in a blender with distilled water (2 times using 500 ml) followed by methanol (2 times using 500 ml) at room temperature and dried in a vacuum at 100° C. for 24 hours. The final oligomeric crystalline poly(aryl ether ketone) having the structural formula (33) was characterized by $^{13}$C NMR and confirmed by mass spectroscopy.

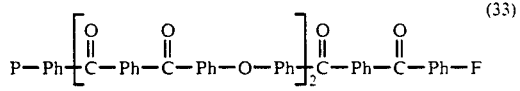

(33)

EXAMPLE 15

A 500 ml flask was fitted with a mechanical stirrer, nitrogen sparge tube, thermometer, reflux condenser, and gas outlet connected to an aqueous sodium hydroxide trap. The apparatus was purged with nitrogen and while under a positive pressure was charged with 40.60 g (0.200 moles) of terephthaloyl chloride, 22.80 g (0.134 moles) of diphenyl ether and 220 mls of 1,2-dichloroethane. The resultant mixture was cooled to 0° C. as 69.34 g (0.520 moles) of aluminum trichloride was added at such a rate as not to exceed 5° C. After stirring for 6 hours at 0° C., 25.75 g (0.268 moles) of fluorobenzene was added and the mixture allowed to warm to 25° C. and stirring continued an additional 17 hours. The entire mixture was then poured into dilute aqueous acid (3000 ml water/100 ml hydrochloric acid conc.) and refluxed with the continuous removal of 1,2-dichloroethane and excess fluorobenzene. The resultant precipitate was collected via filtration, refluxed in 5% hydrochloric acid (700 ml), filtered, washed with water (2 times using 500 ml) followed by methanol (2 times using 500 ml) at room temperature and dried in a vacuum at 100° C. for 24 hours. The final oligomeric crystalline poly(aryl ether ketone) having the structural formula (33) was characterized by $^{13}$C NMR and confirmed by mass spectroscopy.

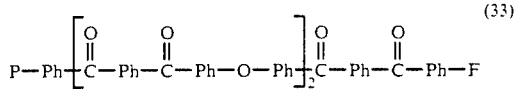

(33)

EXAMPLE 16

A 250 ml glass resin reactor was equipped with a mechanical stirrer, nitrogen sparge tube, thermocouple probe, Dean-Stark trap reflux condenser and a pressure equalizing dropping funnel. To the reactor were charged 2.94 g (0.027 moles) of hydroquinone, 0.19 g (0.001 moles) of potassium carbonate, 2.75 g (0.026 moles) of sodium carbonate, 30.0 g of a difluoro-end-capped crystalline poly(aryl ether ketone) having the general structural formula (29),

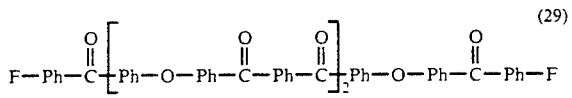

(29)

68.0 g of diphenyl sulfone and xylene. The apparatus was evacuated then charged with nitrogen. This procedure was repeated 4 additional times. While being continuously purged with nitrogen the mixture was heated to 120° C. for 1 hour. The reaction was carried out at a temperature of 320° resulting in a viscous mixture which was poured from the reactor, allowed to solidify and then ground finely. The product was refluxed in acetone (700 ml), followed by an aqueous hydrochloric acid solution (700 ml). It was then washed with water (5 times using 500 ml) and acetone (2 times using 500 ml) at room temperature. The product was dried in a vacuum oven at 100° C. for 24 hours. The final polymer having a general structural formula (30) had a reduced viscosity of 1.75 dl/g (in concentrated sulfuric acid at 1 g/100 ml and 25° C.).

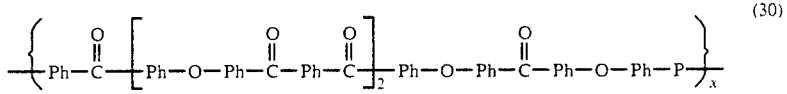

(30)

The polymer was tested as in Example 7. The results are as follows:

| Melt flow ratio | 0.47 |
|---|---|
| Tensile strength (psi) | 14,600 |
| Tensile modulus (psi) | 379,000 |
| Yield elongation (%) | 7.5 |
| Break elongation (%) | 11.2 |
| Pendulum Impact (ft-lb/in³) | 57 |

EXAMPLE 17

A 250 ml glass resin reaction was equipped with a mechanical stirrer, nitrogen sparge tube, thermocouple probe, Dean-Stark trap reflux condenser and a pressure equalizing dropping funnel. To the reactor were charged 1.96 g (0.018 moles) of hydroquinone, 0.13 g (0.001 moles) of potassium carbonate, 1.83 g (0.017 moles) of sodium carbonate, 20.0 g of a difluoro-end-capped crystalline poly(aryl ether ketone) having the general structural formula (29),

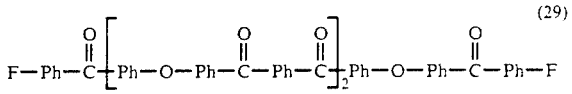

(29)

78.13 g of diphenyl sulfone and xylene. The apparatus was evacuated then charged with nitrogen. This procedure was repeated 3 additional times. While being continuously purged with nitrogen the mixture was heated to 120° C. for 1 hour. The reaction was carried out at a temperature of 320° C. resulting in a viscous mixture which was poured from the reactor, allowed to solidify and then ground finely. The product was refluxed in acetone (700 ml), followed by an aqueous hydrochloric acid solution (700 ml). It was then washed with water (2 times using 500 ml) and acetone (2 times using 500 ml) at room temperature. The product was dried in a vacuum oven at 100° C. for 24 hours. The final polymer having a general structural formula (30) had a reduced viscosity of 1.45 dl/g (in concentrated sulfuric acid at 1 g/100 ml and 25° C.

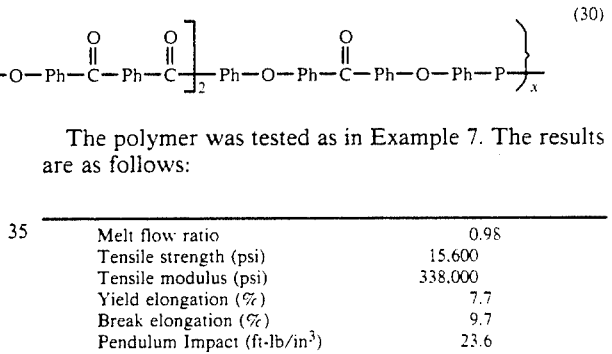

(30)

The polymer was tested as in Example 7. The results are as follows:

| Melt flow ratio | 0.98 |
|---|---|
| Tensile strength (psi) | 15,600 |
| Tensile modulus (psi) | 338,000 |
| Yield elongation (%) | 7.7 |
| Break elongation (%) | 9.7 |
| Pendulum Impact (ft-lb/in³) | 23.6 |

EXAMPLE 18

A 250 ml glass resin reactor was equipped with a mechanical stirrer, nitrogen sparge tube, thermocouple probe, Dean-Stark trap reflux condenser and a pressure equalizing dropping funnel. To the reactor were charged 3.14 g (0.029 moles) of hydroquinone, 0.20 g (0.001 moles) of potassium carbonate, 2.93 g (0.028 moles) of sodium carbonate, 30.0 g of a difluoro-end-capped crystalline poly(aryl ether ketone) having the general structural formula (29),

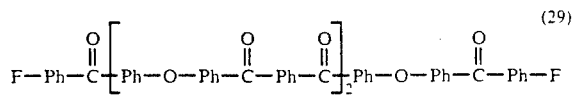

(29)

72.2 g of diphenyl sulfone and xylene. The apparatus was evacuated then charged with nitrogen. This procedure was repeated 3 additional times. While being continuously purged with nitrogen the mixture was heated to 120° C. for 15 minutes. The reaction was carried out at a temperature of 320° resulting in a viscous mixture which was poured from the reactor, allowed to solidify and then ground finely. The product was refluxed in acetone (700 ml), followed by an aqueous hydrochloric acid solution (700 ml). It was then washed with water (2 times using 500 ml) and acetone (2 times using 500 ml) at room temperature. The product was dried in a vacuum oven at 100° C. for 24 hours. The final polymer having a general structural formula (30) had a reduced viscosity of 1.18 dl/g (in concentrated sulfuric acid at 1 g/100 ml and 25° C.

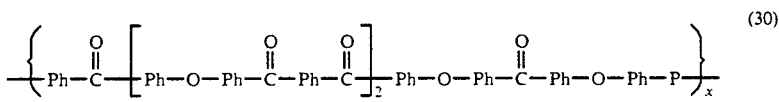
(30)

The polymer was tested as in Example 7. The results are as follows:

| Melt flow ratio | 0.63 |
| Tensile strength (psi) | 15,700 |
| Tensile modulus (psi) | 349,000 |
| Yield elongation (%) | — |
| Break elongation (%) | 7 |

-continued

| Pendulum Impact (ft-lb/in³) | 34 |

What is claimed is:

1. A process for preparing a poly(aryl ether ketone) polymer comprising the following steps:
    (a) reacting (n) moles of HAr H with (n+1) moles of YCOAr₁COY under Friedel-Crafts polymerization conditions to yield

(b) reacting the product obtained in step (a) with 2XAr₂H under Friedel-Crafts polymerization conditions to yield

(c) reacting the product obtained in step (b) with HOAr₃OH in the presence of a base and an aprotic solvent to yield

wherein Ar and Ar₁ are divalent aromatic groups, Ar₂ is a divalent aromatic group wherein the substituents X and CO are in para or ortho position relative to each other, Ar₃ is a residue of a dihydric phenol, X and Y are halogens, n is an integer of 1 to 50 and X is one or greater.

2. A process as defined in claim 1 wherein the ingredients in steps (a) and (b) are simultaneously added to a reactor.

3. A process as defined in claim 1 in which steps (a) and (b) are carried out in the presence of a Friedel-Crafts catalyst.

4. A process as defined in claim 3 wherein the Friedel-Crafts catalyst is selected from aluminum chloride, antimony pentachloride, or ferric chloride.

* * * * *